United States Patent [19]

Caldwell et al.

[11] Patent Number: 4,767,627
[45] Date of Patent: Aug. 30, 1988

[54] DRUG DELIVERY DEVICE WHICH CAN BE RETAINED IN THE STOMACH FOR A CONTROLLED PERIOD OF TIME

[75] Inventors: Larry J. Caldwell; Colin R. Gardner; Robyn C. Cargill, all of Lawrence, Kans.

[73] Assignee: Merck & Co., Inc., Rahway, N.J.

[21] Appl. No.: 44,539

[22] Filed: May 1, 1987

Related U.S. Application Data

[63] Continuation of Ser. No. 738,633, May 29, 1985, abandoned.

[51] Int. Cl.[4] ......................... A61K 9/00; A61K 9/20; A61K 9/48
[52] U.S. Cl. .................................... 424/426; 424/400; 424/422; 424/452
[58] Field of Search ................ 424/400, 422, 426, 452

[56] References Cited

U.S. PATENT DOCUMENTS

| | | | |
|---|---|---|---|
| 3,574,820 | 4/1971 | Johnson et al. | 424/22 |
| 3,797,492 | 3/1974 | Place | 128/260 |
| 3,844,285 | 10/1974 | Laby | 128/260 |
| 3,901,232 | 8/1975 | Michaels et al. | 128/260 |
| 3,976,764 | 8/1976 | Watanabe et al. | 424/19 |
| 3,991,766 | 11/1976 | Schmitt et al. | 424/14 |
| 4,140,755 | 2/1979 | Sheth et al. | 424/21 |
| 4,167,558 | 9/1979 | Sheth et al. | 424/22 |
| 4,207,890 | 6/1980 | Mamajek et al. | 128/223 |
| 4,228,149 | 10/1980 | Brewer et al. | 424/14 |
| 4,268,497 | 5/1981 | Griffin et al. | 424/14 |
| 4,308,250 | 12/1981 | Griffin et al. | 424/14 |
| 4,434,153 | 2/1984 | Urquhart et al. | 424/22 |
| 4,551,329 | 11/1985 | Harris et al. | 424/14 |

Primary Examiner—Shep K. Rose
Attorney, Agent, or Firm—Manfred Polk; Michael C. Sudol

[57] ABSTRACT

A drug delivery device retained in the stomach comprising a planar figure made from an erodible polymer that may release a drug associated therewith over a controlled, predictable and extended period of time.

12 Claims, 3 Drawing Sheets

FIG-1
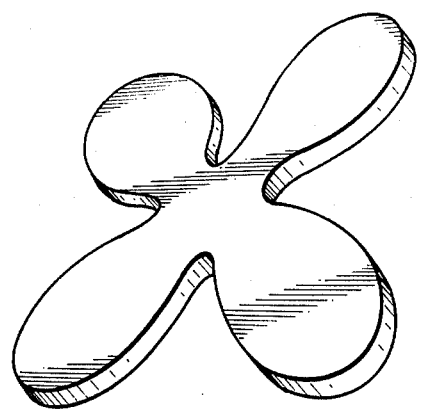
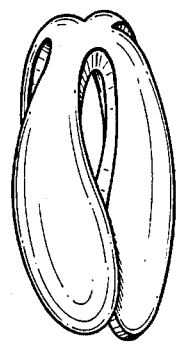
FIG-2a
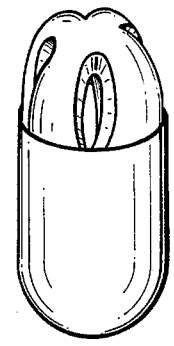
FIG-2b

FIG-3
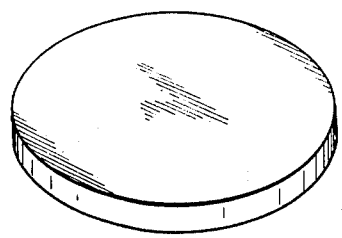
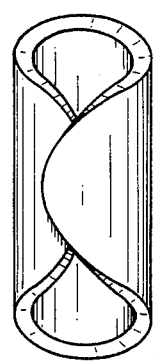 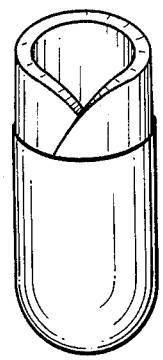
FIG-4a  FIG-4b

FIG-5
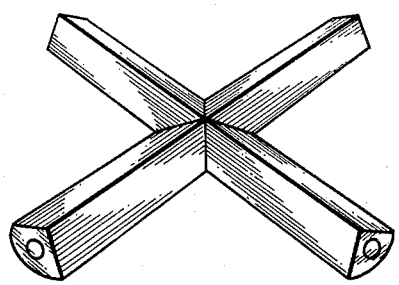
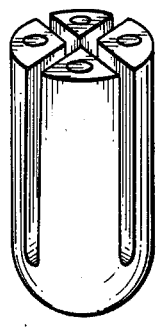     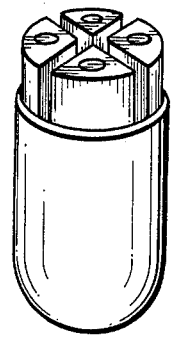
FIG-6a     FIG-6b

DRUG DELIVERY DEVICE WHICH CAN BE RETAINED IN THE STOMACH FOR A CONTROLLED PERIOD OF TIME

This is a continuation, of application Ser. No. 738,633, filed May 29, 1985 now abandoned.

DESCRIPTION OF THE PRIOR ART

Numerous patents and publications have described devices which can be retained in the stomach for extended periods of time. The prior art can be categorically described according to the technologies listed below:
1. Floating devices
2. Swelling devices
3. Inflating balloons and
4. For ruminant animals—various shapes. There follows a discussion of each of the above technologies which demonstrates the technological advancement of the invention over the prior art:

(1) Michaels et al (Alza Corporation), U.S. Pat. No. 3,901,232, describe a device which contains a drug delivery compartment attached to an envelope which is contained within an erodible capsule. Upon ingestion, the capsule dissolves and a liquid contained in the envelope vaporizes and swells the envelope to provide a means of retention by flotation within the desired body cavity e.g. the stomach.

S. Watanabe et al, U.S. Pat. No. 3,976,764 teach the use of a hollow or low density core surrounded by polymeric materials containing drug(s). The device floats in the stomach and releases said drug over an extended period of time.

Sheth and Tossounian, U.S. Pat. Nos. 4,140,755 and 4,167,558 describe the use of a tablet which is hydrodynamically balanced to be buoyant under gastric conditions thereby remaining in the stomach for an extended period of time.

All of the references in this category function on the basis of floatation or buoyancy and do not teach the use of size to retain them in the stomach.

(2) Johnson et al, U.S. Pat. No. 3,574,820 teach the use of tablets or capsules containing a reaction product of gelatin and N-acetyl-homocysteine thiolactone as a component of an oral dosage form small enough to be swallowed but which swells in the stomach to become too large to pass through the pylorus.

Banker, U.S. Pat. No. 261,242 describes the use of a swellable polymer (e.g. Gantrez) coated on the outside of tablets or capsules such that the coating swells under gastric conditions.

Mamajek and Moyer, U.S. Pat. No. 4,207,890 teach the use of an expandable envelope containing a drug and an agent which expands when gastric fluid permeates through the envelope. The device enlarges and is retained in the stomach for an extended period. There is no teaching as to how the device disintegrates or what controls its exit from the stomach.

Theeuwes and Urquhart, U.S. Pat. No. 4,434,153 describe the use of a device (containing a hydrogel) which can enter into the gastrointestinal environment where it imbibes fluid and swells 2–50 fold so that it is retained in the stomach over an extended period. Small pills containing drug are released from this device and subsequently delivered for gastric or intestinal absorption.

The patents of this category teach the use of size to retain the device in the stomach and function by absorption of gastric fluid to cause swelling of an expandable polymeric material. No indication of the obtainable duration is given or of control of the process by which the device disintegrates or otherwise is expelled from the stomach.

(3) Alza Corporation, U.S. Pat. Nos. 3,797,492 and 3,901,232 disclose the use of inflatable bags containing a gas or vapor-generating system to cause inflation following release of the device from a bioerodible capsule in the stomach (or other desired body cavity). The inflated envelope causes the device to be retained in the desired site (e.g. stomach) and drug is released from an attached delivery system. When all the drug has been expelled the envelope deflates and the device passes from the stomach.

These patents imply the use of size to retain the device in the stomach and achieve enlarged size in the stomach via conversion of liquid (or solid) components to a gaseous form. They do not teach the use of mechanical movement to create large forms of the device from a smaller configuration.

(4) R. Laby, U.S. Pat. No. 3,844,285 describes the use of a device having one initial configuration or adapted to be arranged in the configuration so as to pass into the rumen of an animal, whereupon, it changes to a second configuration which will prevent or hinder regurgitation of the device. This patent is applicable to devices which are delivered to the rumen and required to remain in the rumen by preventing regurgitation. The reference does not teach devices designed to enter and be retained in the stomach of humans or other non-ruminant animals. Neither does it teach any procedure for preventing passage of such devices through the pylorus of humans or non-ruminant animals since only regurgitation is hindered or prevented by the device of the reference. The anatomy of the rumen is quite different from that of the stomach of non-ruminant species.

BACKGROUND OF THE INVENTION

The invention provides a drug delivery device comprising at least one drug and a planar disc-shaped or planar multi-lobed figure that is retained in the stomach for predictable and extended periods of time for releasing therapeutic or other beneficial agents.

Many orally administered drugs fail to achieve their full potential because of a number of problems including:
 a. Slow and incomplete intestinal absorption.
 b. Existence of preferential absorption sites in the gastrointestinal tract (absorption windows).
 c. Short biological half-life (in particular if the therapeutic index is low).

Solutions to the delivery problems for these agents cannot be guaranteed using conventional controlled release technology since the site of drug release may be beyond the site of optimal absorption or the transit time through the absorbing portion of the gastrointestinal tract may be too short to effect an increase in the duration of action of the drug. In order to optimize the delivery of these agents to achieve maximum effectiveness (and reduce concentration-related side effects) it is desirable to obtain a drug delivery device which would be retained in the stomach for a prolonged, predictable period of time during which it would release the agent in a predetermined pattern. At the end of its period of usefulness, the device would disintegrate or otherwise alter its properties such that it would exit from the stomach and pass down the intestine.

Accordingly, it is an object of the invention to provide a means of retaining the dosage form in the stomach for an extended, predictable period of time. Thereby the duration of absorption and hence the duration of action of drugs with short biological half-lives could be extended. Likewise the bioavailability of the agents could be improved over that achieved from a conventional dosage form or conventional sustained release preparation.

Another object of the invention is to provide a mechanism whereby after a predetermined time the device will erode, disintegrate or otherwise alter its properties and pass out of the stomach and into the intestine. In addition the device should not lodge in the intestine thereby causing an obstruction.

A further object is to devise a device which will not obstruct the passage of food while the device is in the stomach or after it has passed into the intestine.

Other objects, features and advantages of the invention will be apparent to one skilled in the art from the detailed description of the invention which follows.

A BRIEF DESCRIPTION OF THE DRAWINGS

FIG. 1 is a preferred configuration of the device in a 4-lobed planar form.

FIGS. 2a and 2b show the device of FIG. 1 folded and inserted into a capsule for oral administration.

FIG. 3 is a preferred configuration of the device in a planar, disc-shaped form.

FIGS. 4a and 4b show the device of FIG. 3 folded and inserted into a capsule for oral administration.

FIG. 5 is a preferred configuration of the device in a planar, 4-limbed cross form. Each limb of the device contains a rigid, soluble polymer which slowly erodes resulting in loss of integrity of the device.

FIGS. 6a and 6b show the device of FIG. 5 folded and inserted into a capsule for oral administration.

DESCRIPTION OF THE INVENTION

The invention is directed to a gastric retention device comprising a planar disc-shaped or planar multi-lobed figure prepared from at least one erodible polymer, said device having the following properties:
(a) compressible to a size suitable for swallowing;
(b) expandable to a size which will prevent passage through the pylorus for a predetermined time;
(c) sufficiently resistant to forces by a stomach to prevent passage through a pylorus for a predetermined time; and
(d) erodible in the presence of gastric juices so that said device after a predetermined time is no longer able to retain or attain the expanded configuration defined in (b) above and/or resist the forces as defined in (c) above.

The invention is also directed to a method for the controlled release over a period of time of a drug in the stomach, comprising a planar disc-shaped or planar multi-lobed figure prepared from at least one erodible polymer, said device having the following properties:
(a) compressible to a size suitable for swallowing;
(b) expandable to a size which will prevent passage through a pylorus for a predetermined time;
(c) sufficiently resistable to forces by a stomach to prevent passage through a pylorus for a predetermined time; and
(d) erodible in the presence of gastric juices so that said device after a predetermined time is no longer able to retain or attain the expanded configuration defined in (b) above and/or resist the forces as defined in (c) above.

Definitions

Gastric retention device is a device which resides in the confines of the stomach for the purpose of providing a platform for controlled release of biologically active agents.

A planar disc-shaped or multi-lobed flat or planar device may be used which is large enough and rigid enough such that said device will not pass out of the stomach but will allow passage of food around said device. Preferred configurations are illustrated in FIGS. 1-6.

The longest diameter (the device need not be symmetrical) of the device may vary between 1.6 and 5 cm; more preferably in the range 2.0 to 4 cm; and most preferably in the range 3.2 to 3.6 cm.

The expanded devices shown in FIGS. 1, 3 and 5 are compressed by folding or rolling to subsequently obtain the form of FIGS. 2a, 4a, and 6a respectively and ultimately inserted into capsules as illustrated in FIGS. 2b, 4b and 6b.

Criterion A means that the desired expanded configuration of said device is too large to be swallowed and thus must be compressed and contained in a conventional capsule or like container for swallowing. The capsule is designed to dissolve after oral ingestion within the confines of the stomach.

Criterion B means that after the compressed device within the capsule container reaches the stomach, upon dissolution and/or disintegration of the retaining capsule or like container, said device will expand or unfold in such a manner that results in its original shape which is too large to pass from the stomach into the intestine unless enough force is applied to recompress the device. This "expanded" form of the device will remain in the stomach for a pre-determined period of time depending on the desired time profile of release of the biologically active agent, which is a part of the device or contained within a controlled release module that is attached to the retention device. The "pre-determined time" is preferably within the range of 1 hour to 1 year. For example, a biologically active agent which prevents heartworm infestation in dogs might require gastric retention and controlled delivery of said agent over the course of 6-12 months. This period depends on the seasonal changes of the mosquito population which is the main vector of heart worm infection in dogs. A second example is the use of such a gastric retention device to maintain controlled delivery of a contraceptive agent. The desired retention time of the device might be 3-4 weeks to coincide with the normal frequency of menses. A third example is the use of such a device to achieve once daily dosing, if such device is coupled to a controlled release device for delivery of an agent with a very short half-life of biological activity, such as a dopamine agonist for treatment of Parkinsonism.

Criterion C means that the device in question must sustain some compressive force, in excess of that amount the stomach is able to apply, in order for said device to not prematurely pass on into the intestine. For humans and animals with similar gastric anatomy such as dogs, the gastric pouch is capable of applying forces of 50-150 grams.

Criterion D means that after some predetermined time, during which said device has been utilized, some part of the device will suddenly or gradually fail to meet Criteria B and/or C. That is, the device will either be unable to withstand a lesser compressive force, or will lose its integrity as a single unit, and thereby be subject to the normal propulsive forces and pass out of the stomach. By doing so, the danger of multiple devices causing obstructive problems, is obviated.

These devices can be manufactured by a number of processes including injection molding, extrusion, film-forming, laminating and the like as will be clear to one skilled in the art. For example, a mold cn be constructed in the desired shape of the device and filled with appropriate material(s) in the liquid state and then allowed to cure by chemical processes or cooling if thermosetting material(s) is used.

A critical property of the devices is that, after a certain, pre-determined period of time in the stomach they will alter their properties in a manner which will permit their elimination from the stomach into the intestine. For this purpose the devices must contain component(s), sections(s) or points(s) which will erode or dissolve in the aqueous environment of the stomach.

For example, the four lobes of the device of FIG. 1 may be fastened at a central point by glue (or other material) which will dissolve or erode during the desired time period, thereby liberating the individual lobes which will then easily pass out of the stomach.

The disc can be manufactured from composite materials such that one or more component(s) will erode or dissolve leaving a disc whose mechanical properties are such that it can be readily removed from the stomach by the compression forces associated with the recurrent interdigestive migratory myoelectric complex.

A further modification of the four-lobed form is to have contained within the lobes an erodible or dissolving structure which will maintain the lobes in a rigid configuration until the internal, structurally supporting material has disintegrated. At that point the device would be incapable of maintaining its rigid, planar conformation and would be eliminated from the stomach. (see FIG. 3 and Example 2)

Likewise these devices can be manufactured from materials which are entirely erodible.

Representative erodible polymers which can be employed in the practice of the invention are cellulosics such as Klucel (hydroxypropylcellulose), cellulose acetate phthalate, methyl cellulose, hydroxypropylmethylcellulose phthalate and the like; ethylene/vinyl alcohol copolymer; ethylenemaleic anhydride copolymer; polyacrylates such as Eudragit E (cationic copolymer based on dimethylaminoethyl methylacrylate and neutral methylacrylic acid esters), poly(acrylic acid), poly(methacrylic acid) and the like; polylactones such as poly(caprolactone) and the like; polyanhydrides such as poly[bis-(p-carboxyphenoxy)propane anhydride], poly(terephthalic acid anhydride) and the like; polyvinyl pyrrolidone; polyamides and polypeptides such as polylysine, polyglutamic acid and the like; gelatin and derivatives such as those produced on reaction with N-acetyl-homo-cysteine thiolactone and the like; polyesters such as polylactides, polyglycolides, poly(betahydroxybutyric acid) and the like; poly(ortho esters) such as copolymers of DETOSU with diols such as hexane diol, decane diol, cyclohexane dimethanol, ethylene glycol, polyethylene glycol and incorporated herein by reference those poly(ortho) esters described and disclosed in U.S. Pat. No. 4,304,767 and the like; polyurethanes such as those prepared with poly(tetramethylene oxide), prepolymer terminated with hexamethylene diisocyanate and a poly functional diester of oxalic acid and glycerol, di-(2,3-dihydroxypropyl)oxalate or its mixture with 3,6-dioxaoctane-1,8-diol and the like; polyacrylonitriles such as poly(alkyl-α-cyanoacrylates) wherein the alkyl is methyl, ethyl, propyl, butyl, amyl and the like; and types of inorganic glass based on polyphosphates and fused salts.

Representative non-erodible polymers that may be employed in the practice of the invention are polyolefins such as polyethylene, polypropylene, ethylene vinyl acetate copolymers, poly(tetrafluoroethylene) and the like; rubbers such as silicon based rubber, styrene-butadiene copolymers and the like polyamides such as nylon 6,6, nylon 6, and the like; polyesters such as poly(ethylene terephthalate) and the like; polyurethanes formed from diisocyanates such as 1,6-hexane diisocyanate or biphenylene diisocyanate etc. and diols such as ethylene glycol, 1,4-butane diol and the like; and cellulosics such as ethyl cellulose, cellulose diacetate, cellulose triacetate and the like.

A drug or medicament may be associated with the gastric retention device in different ways, depending on the physical and chemical properties of the drug or medicament. For example, the drug may be dispersed as a solution or suspension within an erodible polymer matrix such that as the matrix erodes within the confines of the gastric pouch, the drug is released at a predetermined rate. Similarly, the drug may be dissolved or dispersed within a non-erodible matrix material comprising part of the retention device. As this matrix comes in contact with gastric fluid, the drug diffuses out of the non-erodible matrix at a predetermined rate. An alternative to incorporating the drug as an integral part of the gastric retention device is to simply fasten a controlled release drug module to the retention device. Such a module might be a miniature constant-flow pump, either mechanically or osmotically driven, and may be fastened to the retention device by gluing or tethering. Likewise it may consist of a matrix system, erodible or non-erodible, fastened to the retention device.

In man and similarly-sized non-ruminate mammals, the size of the pyloric valve between the stomach and small intestine is generally in the range of 3–5 cm maximum inner circumference. Objects with a mimimum circumference of more than 5 cm will generally not pass from the stomach through the pylorus. The devices described herein are designed to present a minimum circumference of more than 5 cm after deployment in the stomach. Before deployment in the stomach the minimum circumference is less than 2 cm.

The active agents (therapeutic agent or other beneficial agents) which can be utilized in accordance with the practice of the invention is not critical. Any agent which can be obtained in a stable form is applicable herein. As to the amount of active agent which can be delivered in accordance with the invention, said amount depends on a variety of factors such as the host, physical attributes, particular disease or disorder being treated and of course the severity of the condition being treated. The amount of active agent utilizable in the invention is known to one skilled in the art and is disclosed in various medical references such as PDR and etc. or could be obtained from suitably designed clinical trials.

Generally, the amount of polymer employed in the practice of the invention ranges from 10% to 99.9% polymer (preferably 20% to 60%) by weight of the drug delivery platform. The remaining portion of the composition contains the medicament and conventional pharmaceutically acceptable excipients.

Representative pharmaceutically acceptable excipients that the drug delivery device may contain are buffering agents and preservatives. Suitable water soluble preservatives which may be employed in the drug delivery device are sodium bisulfite, sodium thiosulfate, ascorbate, benzalkonium chloride, chlorobutanol, thimerosal, phenylmercuric borate, parabens, benzyl alcohol and phenylethanol. These agents may be present in amounts from 0 to 5% by weight. Suitable water soluble buffering agents are alkali or alkali earth carbonates, phosphates, bicarbonates, citrates, borates, acetates, acid anhydrides, succinates and the like, such as sodium phosphate, citrate, borate, acetate, bicarbonate and carbonate. These agents may be present in amounts sufficient to maintain some optimum pH of the system in the range 1 to 9. As such the buffering agent can be as much as 25% on a weight to weight basis of the total composition.

The following examples illustrate the preparation of various drug delivery devices of the invention. The Examples should be construed as illustrations rather than limitations thereof.

EXAMPLE 1

Studies were performed with Beagle dogs in order to ascertain gastric retention time of the drug delivery device described herein. The parameters investigated were size, shape and erodibility. These devices were administered in gelatin capsules and their position in the gastrointestinal tract determined using x-ray techniques.

The results for disc and 4-lobed planar devices of different dimensions and made from Silastic (Dow Company) medical grade silicone rubber labelled with 15% barium sulfate are shown below.

| Shape | Dimensions | % Retained at 24 hrs. | N* |
|---|---|---|---|
| Disc | 2.5 cm diameter | 67 | 9 |
| 4-lobed figure | 3.2 cm diameter | 90 | 10 |
|  | 2.7 cm diameter | 83 | 12 |
|  | 2.2 cm diameter | 60 | 10 |

*Number of trials

These data indicate that the retention of these devices in the stomach is a function of their diameter and that retention for a period of 24 hours is possible using devices which can be folded into gelatin capsules suitable for swallowing.

EXAMPLE 2

The effect of erosion on the performance of one of the devices is demonstrated in this example. The planar cross form shown in FIG. 5 was constructed containing segments of rigid, bioacceptable material. For this example segments of spaghetti were inserted into hollows in the limbs of the cross. When the device came into contact with water, the spaghetti segments absorbed water and lost their rigidity. The overall effect was to produce a device which had lost its integrity and which could be more readily expelled from the stomach by the forces of the interdigestive migratory myoelectric complex. The data from one such experiment using Beagle dogs are shown below.

| Shape | % Retained in stomach at 24 hrs. | N |
|---|---|---|
| cross with non-eroding limbs | 100% | 2 |
| cross with eroding limbs (spaghetti) | 71% | 7 |
| cross with empty limbs | 57% | 7 |

The data show that the cross-form with hollow limbs is much less-well retained than the same shape with rigid, non-eroding limbs. The device with initially rigid, but eroding, limbs was intermediate in performance.

What is claimed is:

1. A gastric retention device comprising a gelatin capsule having squeezed together and compressed therein a hollow limbed 4-lobed planar cross figure prepared from at least one erodible polymer, selected from the group consisting of soluble cellulosic materials, ethylene vinyl alcohol, elthylene maleic anhydride copolymer, polyacrylates, polycaprolactones, inorganic glass based on polyphosphates and fused salts, polyanhydrides, poly(ortho)esters, biodegradable polyurethanes, polyvinyl pyrrolidone, polyactones, polyamides and polypeptides, gelatin and derivatives, polyacrylonitriles, polyesters and combinations thereof; said device having a biological active drug dispersed as a solution or suspension incorporated therein or in a module attached to the retention device, consisting of a frame work having a maximum dimension of 1.6 cm before deployment and presenting a minimum diameter of 1.6 cm and a maximum diameter of 5 cm after deployment into the stomach of man and non-ruminant mammals, composed in a manner such that the frame work will not pass the stomach having a pyloric valve with a 3–5 cm maximum inner circumference between the stomach and the intestine, said figure having the following properties:

(a) compressible to a size suitable for swallowing;
(b) expandable to size which will prevent passage through a pylorus for a predetermined time;
(c) sufficiently resistant to a simultaneous force in two directions by a stomach to prevent passage through a pylorus for a predetermined time; and
(d) erodible in the presence of gastric juices so that said device after a predetermined time is no longer able to retain or attain the expanded configuration defined in (b) above and/or resist a simultaneous force in two directions as defined in (c) above.

2. The device of claim 1, wherein said planar figure is prepared from at least one erodible polymer and at least one non-erodible polymers selected from the group consisting of polyolefins, ethylenevinylacetate copolymers, rubbers, ethylenevinylalcohol copolymers, polyamides, polyurethanes, polyesters, teflon, non-water-soluble cellulosic and combinations thereof.

3. The device of claim 1, wherein said planar figure is from 1.6 to 5 cm in diameter; wherein said erodible polymer is selected from the group consisting of polyolefins, ethylenevinylacetate copolymer, ethylenevinylalcohol copolymer, poly(ortho)esters, cellulosics, polyanhydrides, polyamides and polypeptides, polyphosphates and fused salt and combinations, blends and copolymers thereof; and wherein said predetermined time is from one (1) hour to one (1) year.

4. The device of claim 3, wherein said polyolefin is polyethylene or polypropylene; and said cellulosic is hydroxypropylcellulose, cellulose acetate phthalate or ethyl cellulose.

5. The device of claim 3, wherein said planar figure is from 2 to 4 cm in diameter said polymer is selected from the group consisting of a mixture of poly(ortho) ester/polyethylene, a mixture of ethylene/vinylacetate, poly(ortho) ester and polyethylene; and said predetermined time is from 16 to 48 hours.

6. The device of claim 5 wherein said polymer is a mixture of poly(ortho ester) and polyethylene.

7. The device of claim 6 wherein said mixture is 75/25 poly(ortho ester)/polyethylene.

8. The device of claim 1 wherein said polymer is a poly(ortho) ester.

9. A method for the controlled release over a period of time of a drug in the stomach by administering a gastric retention device comprising a gelatin capsule having squeezed together and compressed therein a hollow limbed 4-lobed planar cross figure prepared from at least one erodible material selected from the group consisting of soluble cellulosic materials, ethylene vinylalcohol, ethylene maleic anhydride copolymer, polyacrylates, polycaprolactones, inorganic glass based on polyphosphates and fused salts, polyanhydrides, poly(ortho)esters, biodegradable polyurethanes, polyvinyl pyrrolidone, polyactones, polyamides and polypeptides, gelatin and derivatives, polyacrylonitriles, polyesters and combinations thereof; said device having a biological active drug dispersed as a solution or suspension incorporated therein or in a module attached to the retention device, consisting of a frame work having a maximum dimension of 1.6 cm before deployment and presenting a minimum diameter of 1.6 cm and a maximum diameter of 5 cm after deployment into the stomach of man and non-ruminant mammals, composed in a manner such that the frame work will not pass the stomach having a pyloric valve with a 3-5 cm maximum inner circumference between the stomach and the intestine, said figure having the following properties:
  (a) compressible to a size suitable for swallowing;
  (b) expandable to size which will prevent passage through a pylorus for a predetermined time;
  (c) sufficiently resistant to a simultaneous force in two directions by a stomach to prevent passage through a pylorus for a predetermined time; and
  (d) erodible in the presence of gastric juices so that said device after a predetermined time is no longer able to retain or attain the expanded configuration defined in (b) above and/or resist a simultaneous force in two directions as defined in (c) above.

10. The method of claim 9, wherein said planar figure is prepared from at least one erodible polymer and at least one non-erodible polymer selected from the group consisting of polyolefins, ethylenevinylacetate copolymers, rubbers, ethylenevinylalcohol copolymers, polyamides, polyurethanes, polyesters, teflon, non-water-soluble cellulosic and combinations thereof.

11. The method of claim 9, wherein said planar figure is from 1.6 to 5 cm in diameter wherein said erodible polymer is selected from the group consisting of polyolefins, ethylenevinylacetate copolymer, ethylenevinylalcohol copolymer, poly(ortho)esters, cellulosics, polyanhydrides, polyamides and polypeptides, polyphosphates and fused salts and combinations, blends and copolymers thereof; and wherein said predetermined time is from one (1) hour to one (1) year.

12. The method of claim 9 wherein said planar figure is from 2 to 4 cm in diameter; said polymer is selected from the group consisting of a mixture of poly(ortho ester)/polyethylene, a mixture of ethylene/vinylacetate, poly(ortho ester) and polyethylene; and said predetermined time is from 16 to 48 hours.

* * * * *